(12) United States Patent
Bernardelli et al.

(10) Patent No.: US 7,429,598 B2
(45) Date of Patent: *Sep. 30, 2008

(54) SPIROCONDENSED QUINAZOLINONES AND THEIR USE AS PHOSPHODIESTERASE INHIBITORS

(75) Inventors: Patrick Bernardelli, Sandwich (GB); Fabrice Vergne, Sandwich (GB); Chrystelle Mendes, Sandwich (GB); Pierre G. Ducrot, Sandwich (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/667,111

(22) Filed: Sep. 17, 2003

(65) Prior Publication Data

US 2004/0106631 A1     Jun. 3, 2004

Related U.S. Application Data

(60) Provisional application No. 60/429,507, filed on Nov. 26, 2002.

(30) Foreign Application Priority Data

Sep. 17, 2002  (EP) ................. 02292275

(51) Int. Cl.
*A61K 31/517* (2006.01)
*C07D 487/12* (2006.01)
*C07D 487/14* (2006.01)

(52) U.S. Cl. .............. 514/266.3; 514/267; 514/278; 544/231

(58) Field of Classification Search ........... 514/212.02, 514/266.2, 266.3, 267, 278; 544/231, 249
See application file for complete search history.

(56) References Cited

U.S. PATENT DOCUMENTS 4,666,913 A * 5/1987 Kubla et al. .............. 514/266.2
4,764,512 A * 8/1988 Molino et al. ............. 514/183
4,906,630 A * 3/1990 Studt et al. ............... 514/252.02
2002/0198198 A1* 12/2002 Bernardelli et al. ....... 514/224.2

FOREIGN PATENT DOCUMENTS

| EP | 530994 | * | 3/1993 |
|---|---|---|---|
| EP | 530994 A1 | * | 3/1993 |
| JP | 59-59685 A | | 4/1984 |
| RU | 2110518 C1 | | 5/1998 |
| WO | WO8801508 | | 3/1988 |
| WO | WO 92/06975 A1 | | 4/1992 |
| WO | WO0066560 | | 9/2000 |
| WO | WO 02/074754 A1 | | 9/2002 |
| WO | WO 02/076593 A1 | | 10/2002 |

OTHER PUBLICATIONS

Kyowa Hakko Kogyo Co Ltd, "Novel Piperidine Derivative and its Preparation", Patent Abstracts of Japan, Pub No. 59-059685, Publ. Date Apr. 5, 1984 (Abstract of JP-59-59685 A).
Martinez, et al., "Benzyl Derivatives of 2, 1, 3-Bnezo- and Benzothieno '3, 2-athiadiazine 2, 2-Dioxides: First Phosphodiesterase 7 Inhibitors", J Med Chem, 2000, pp. 683-689, vol. 43, No. 4.
Wright, L. et al., "Phosphodiesterase Expression in Human Epithelial Cells", Amer J Physiology Lung Cell Mol Physiol, 1998, pp. L694-L700, vol. 275.

* cited by examiner

*Primary Examiner*—James O. Wilson
*Assistant Examiner*—Tamthom N Truong
(74) *Attorney, Agent, or Firm*—Gregg C. Benson

(57) ABSTRACT

The invention relates to compounds of formula (I)

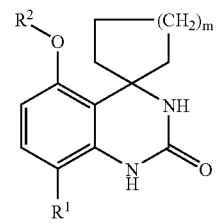

wherein $R^1$, $R^2$ and m are as defined in the description, their use as medicament, pharmaceutical compositions containing them and a process for their preparation.

10 Claims, No Drawings

SPIROCONDENSED QUINAZOLINONES AND THEIR USE AS PHOSPHODIESTERASE INHIBITORS

FIELD OF THE INVENTION

The invention relates to spirotricyclic derivatives, the process for their preparation, and their use as phosphodiesterase inhibitors.

BACKGROUND OF THE INVENTION

Phosphodiesterases (PDE) play an important role in various biological processes by hydrolysing the key second messengers adenosine and guanosine 3',5'-cyclic monophosphates (cAMP and cGMP respectively) into their corresponding 5'-monophosphate nucleotides. Therefore, inhibition of PDE activity produces an increase of cAMP and cGMP intracellular levels that activate specific protein phosphorylation pathways involved in a variety of functional responses. At least eleven isoenzymes of mammalian cyclic nucleotide phosphodiesterases, numbered PDE 1 through PDE 11, have been identified on the basis of primary structure, substrate specificity or sensitivity to cofactors or inhibitory drugs.

Among these phosphodiesterases, PDE7 is a cAMP-specific PDE. The biochemical and pharmacological characterization showed a high-affinity cAMP-specific PDE (Km=0.2 μM), that was not affected by cGMP potent selective PDE isoenzyme inhibitors.

PDE7 activity or protein has been detected in T-cell lines, B-cell lines, airway epithelial (AE) cell lines and several foetal tissues.

Increasing cAMP levels by selective PDE7 inhibition appears to be a potentially promising approach to specifically block or modulate T-cell and B-cell mediated immune responses. Further studies have demonstrated that elevation of intracellular cAMP levels can modulate inflammatory and immunological processes. This selective approach could presumably be devoid of the side effects associated with known selective PDE inhibitors (e.g. PDE3 or PDE4 selective inhibitors) and which limit their use.

A functional role of PDE7 in T-cell activation has also been disclosed; therefore selective PDE7 inhibitors are candidates for the treatment of T-cell-related diseases.

AE cells actively participate in inflammatory airway diseases by liberating mediators such as arachidonate metabolites and cytokines. Selective inhibition of PDE7 may be a useful anti-inflammatory approach for treating AE cells related diseases. B cells are well known key players in the allergic response, then selective PDE7 inhibitors are candidates for the treatment of B-cell-related diseases.

Thus, there is a need for selective PDE7 inhibitors, which are active at very low concentrations, i.e. preferably nanomolar inhibitors.

WO 88/01508 discloses compounds of formula

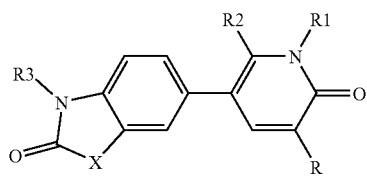

where R is H, alkyl, alkoxyalkyl, hydroxyalkyl, halo, cyano, carbamoyl, alkyl carbamoyl, formyl, alkylamino or amino;
X is —(CR4R5)a-NR6-(CR4R5)b-;
R1, R2, R3, and R5 are H or alkyl;
R4 and R6 are H, alkyl or aralkyl; a and b are 0, 1 or 2 and a+b=0, 1 or 2; R4 and R5 groups on vicinal carbon atoms may together form a carbon-carbon double bond; and geminal R4 and R5 groups may together form a spiro substitutent, —(CH2)d-, where d is 2 to 5; or a pharmaceutically acceptable salt thereof. These compounds are described as cardiotonics.

WO 00/66560 discloses compounds of formula

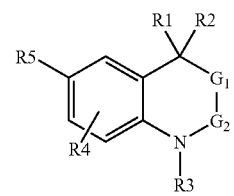

These compounds are described as progesterone receptor modulators.

SUMMARY OF THE INVENTION

The present invention provides compounds, which are PDE inhibitors, preferably PDE7 inhibitors, of formula (I)

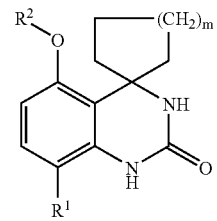

wherein,
m is 1, 2 or 3, and,
$R^1$ is selected from $CH_3$, Cl, Br and F and,
$R^2$ is selected from,
- $Q^1$-$Q^2$-$Q^3$-$Q^4$ wherein,
  $Q^1$ is a single bond or a linear or branched ($C_1$-$C_6$) alkylene group;
  $Q^2$ is a saturated 4 to 6-membered heterocycle comprising one or two heteroatoms selected from O or N;
  $Q^3$ is a linear or branched ($C_1$-$C_6$)alkylene group;
  $Q^4$ is a 4 to 8-membered, aromatic or non aromatic, heterocycle comprising 1 to 4 heteroatoms selected from O, S, S(=O), $SO_2$ and N, said heterocycle being optionally substituted with one or several groups, preferably one, selected from OR, NRR', CN and ($C_1$-$C_6$)alkyl, wherein R and R' are the same or different and are selected from H and ($C_1$-$C_6$)alkyl;
  the atom of $Q^2$ bound to $Q^1$ is a carbon atom, and,
  the atom of $Q^4$ bound to $Q^3$ is a carbon atom;
- ($C_1$-$C_6$)alkyl, said alkyl group being substituted with 1 to 3 groups, preferably 1, selected from $OR^4$, $COOR^4$, $NR^4R^5$, $NRC(=O)R^4$, $C(=O)NR^4R^5$ and $SO_2NR^4R^5$, wherein, R is H or $(C_1-C_6)$alkyl;

$R^4$ is $(C_1-C_6)$alkyl substituted with one or several groups, preferably 1 to 3, selected from F, CN, $S(=O)R^6$, $SO_3H$, $SO_2R^6$, $SR^7$, $C(=O)$—NH—$SO_2$—$CH_3$, $C(=O)R^7$, $NR'C(=O)R^7$, $NR'SO_2R^6$, $C(=O)NR^7R^8$, O—$C(=O)NR^7R^8$ and $SO_2NR^7R^8$, wherein R' is H or $(C_1-C_6)$alkyl, $R^6$ is $(C_1-C_6)$alkyl optionally substituted with one or two groups OR" wherein R" is selected from H and $(C_1-C_6)$alkyl and $R^7$ and $R^8$ are the same or different and are selected from H and $R^6$;

$R^5$ is selected from $R^4$, H and $(C_1-C_6)$alkyl; or, said alkyl group being 1) substituted with 1 to 3 groups, preferably 1, selected from $OC(=O)R^4$, $SR^4$, $S(=O)R^3$, $C(=NR^9)R^4$, $C(=NR^9)$—$NR^4R^5$, NR-C$(=NR^9)$-$NR^4R^5$, $NRCOOR^4$, NR—$C(=O)$—$NR^4R^5$, $NR-SO_2$—$NR^4R^5$, $NR-C(=NR^9)$-$R^4$ and $NR-SO^2$-$R^3$ and, 2) optionally substituted with 1 or 2 groups selected from $OR^4$, $COOR^4$, $C(=O)$-$R^4$, $NR^4R^5$, $NRC(=O)R^4$, $C(=O)NR^4R^5$ and $SO_2NR^4R^5$;

wherein,

R is selected from H and $(C_1-C_6)$alkyl;

$R^9$ is selected from H, CN, OH, $OCH_3$, $SO_2CH_3$, $SO_2NH_2$ and $(C_1-C_6)$alkyl, and, $R^3$ is $(C_1-C_6)$alkyl, unsubstituted or substituted with one or several groups, preferably 1 to 3, selected from F, CN, $S(=O)R^6$, $SO_3H$, $SO_2R^6$, $C(=O)$—NH—$SO_2$—$CH_3$, $OR^7$, $SR^7$, $COOR^7$, $C(=O)R^7$, O—$C(=O)NR^7R^8$, $NR^7R^8$, $NR'C(=O)R^7$, $NR'SO_2R^6$, $C(=O)NR^7R^8$ and $SO_2NR^7R^8$, wherein R' is H or $(C_1-C_6)$alkyl, $R^6$ is $(C_1-C_6)$alkyl optionally substituted with one or two groups OR", wherein R" is selected from H and $(C_1-C_6)$alkyl and $R^7$ and $R^8$ are the same or different and are selected from H and $R^6$;

$R^4$ and $R^5$ are the same or different and are selected from H and $R^3$;

or their racemic forms, their isomers and their pharmaceutically acceptable derivatives.

These compounds are selective PDE7 inhibitors. They can be used in the treatment of various diseases, such as T and B-cell-related diseases, autoimmune diseases, osteoarthritis, rheumatoid arthritis, multiple sclerosis, osteoporosis, chronic obstructive pulmonary disease (COPD), asthma, allergic rhinitis, allergy, cancer such as leukemia, acquired immune deficiency syndrome (AIDS), allergy, inflammatory bowel disease (IBD), ulcerative colitis, Crohn's disease, pancreatitis, dermatoses such as psoriasis and atopic dermatitis, glomerulonephritis, conjunctivitis, autoimmune diabete, graft rejection, epilepsy, muscular atrophy or systemic lupus erythematosus.

The invention further relates to a compound of formula (I) as a medicament.

The invention further concerns the use of a compound of formula (I) for the manufacture of a medicament for the prevention or the treatment of disorders for which therapy by a PDE7 inhibitor is relevant.

The invention also provides a method for the treatment of a disorder for which therapy by a PDE7 inhibitor is relevant, comprising administering to a mammal in need thereof an effective amount of compound of formula (I).

The invention also concerns a pharmaceutical composition comprising a compound of formula (I) together with a pharmaceutically acceptable carrier, excipient, diluent or delivery system.

The invention also relates to a process for the preparation of compounds of formula (I).

DETAILED DESCRIPTION OF THE INVENTION

The present invention provides compounds, which are PDE7 inhibitors, having formula (I)

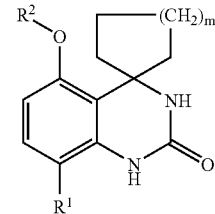

wherein $R^1$, $R^2$ and m are as defined above.

A preferred group of compounds of formula (I) is the one in which $R^2$ is $(C_1-C_6)$alkyl, said alkyl group being substituted with a group selected from $OR^4$, $COOR^4$, $NR^4R^5$, $NRC(=O)R^4$, $C(=O)NR^4R^5$ and $SO_2NR^4R^5$, wherein, R is H or $(C_1-C_6)$alkyl;

$R^4$ is $(C_1-C_6)$alkyl substituted with 1 to 3 groups selected from $S(=O)R^6$, $SO_2R^6$, $NR'C(=O)R^7NR'SO_2R^6$, $C(=O)NR^7R^8$, O—$C(=O)NR^7R^8$ and $SO_2NR^7R^8$, wherein $R^6$ is $(C_1-C_6)$alkyl and R', $R^7$ and $R^8$ are the same or different and are selected from H and $(C_1-C_6)$alkyl;

$R^5$ is selected from $R^4$, H and $(C_1-C_6)$alkyl.

Preferably, $R^2$ is $(C_1-C_4)$alkyl, said alkyl group being substituted with a group $NR^4R^5$ or $C(=O)NR^4R^5$, wherein, $R^4$ is $(C_1-C_6)$alkyl substituted with a group selected from $S(=O)CH_3$, $NHC(=O)CH_3$ and $C(=O)NR^7R^8$, wherein $R^7$ and $R^8$ are the same or different and are selected from H and methyl;

$R^5$ is selected from H and methyl.

Another preferred group of compounds of formula (I) is the one in which $R^2$ is $(C_1-C_6)$alkyl, said alkyl group being 1) substituted with 1 to 3 groups, preferably 1, selected from $OC(=O)R^4$, $SR^4$, $S(=O)R^3$, $NRCOOR^4$, $NR-C(=O)$—$NR^4R^5$, $NR-SO_2$—$NR^4R^5$ and $NR-SO^2$-$R^3$ and, 2) optionally substituted with OH or $OCH_3$;

wherein,

R is selected from H and $CH_3$;

$R^3$ is $(C_1-C_6)$alkyl, unsubstituted or substituted with 1 to 3 groups, selected from F, CN, $S(=O)R^6$, $SO_3H$, $SO_2R^6$, $C(=O)$—NH—$SO_2$—$CH_3$, $OR^7$, $SR^7$, $COOR^7$, $C(=O)R^7$, O—$C(=O)NR^7R^8$, $NR^7R^8$, $NR'C(=O)R^7$, $NR'SO_2R^6$, $C(=O)NR^7R^8$ and $SO_2NR^7R^8$, wherein $R^6$ is $(C_1-C_6)$alkyl and R1, $R^7$ and $R^8$ are the same or different and are selected from H and $(C_1-C_6)$alkyl;

$R^4$ and $R^5$ are the same or different and are selected from H and $R^3$.

Preferably, $R^2$ is $(C_1-C_6)$alkyl substituted with $S(=O)R^3$ wherein $R^3$ is $(C_1-C_6)$alkyl, optionally substituted with 1 to 3 groups selected from $S(=O)R^6$, $SO_2R6$, $NR^7R^8$, $OR^7$, $NR'C(=O)R^7$, $NR'SO_2R^7$, $C(=O)NR^7R^8$ and O—$C(=O)NR^7R^8$, wherein $R^6$ is $(C_1-C_6)$alkyl and R', $R^7$ and $R^8$ are the same or different and are selected from H and $(C_1-C_6)$alkyl.

Preferably, $R^2$ is $(C_1-C_6)$alkyl substituted with $S(=O)R^3$ wherein $R^3$ is $(C_1-C_6)$alkyl, preferably methyl.

Another preferred group of compounds of formula (I) is the one in which $R^2$ is $Q^1-Q^2-Q^3-Q^4$ wherein, $Q^1$ is a single bond or a linear or branched $(C_1-C_6)$alkylene group;

$Q^2$ is a saturated 4 to 6-membered heterocycle comprising a nitrogen atom;

$Q^3$ is a linear $(C_1-C_4)$alkylene group;

$Q^4$ is a 5 or 6-membered, aromatic heterocycle comprising 1 to 4 nitrogen atoms, said heterocycle being optionally substituted with a methyl;

the atom of $Q^2$ bound to $Q^1$ is a carbon atom, and, the atom of $Q^4$ bound to $Q^3$ is a carbon atom.

Preferably, $R^2$ is $Q^1-Q^2-Q^3-Q^4$ wherein, $Q^1$ is a single bond;

$Q^2$ is a saturated 4 to 6-membered heterocycle comprising a nitrogen atom, preferably azetidine;

$Q^3$ is $-CH_2-$;

$Q^4$ is a 5-membered, aromatic heterocycle comprising 2 nitrogen atoms, said heterocycle being optionally substituted with a methyl;

the atom of $Q^2$ bound to $Q^1$ is a carbon atom, and, the atom of $Q^4$ bound to $Q^3$ is a carbon atom.

In each group of compounds defined above, the following substitutions are further preferred:

$R^1$ is Cl or F.

m is 2.

Preferably $R^1$ is Cl or F and m is 2.

The following compounds are particularly preferred:

5'-(2-[(2-amino-2-oxoethyl)amino]ethoxy)-8'-chloro-1'H-spiro[cyclohexane-1,4'-quinazolin]-2'(3'H)-one;

8'-chloro-5'-([methylsulfinyl]methoxy)-1'H-spiro[cyclohexane-1,4'-quinazolin]-2'(3'H)-one;

5'-(2-{[2-(acetylamino)ethyl]amino} ethoxy)-8'-chloro-1'H-spiro[cyclohexane-1,4'-quinazolin]-2'(3'H)-one;

8'-fluoro-5'-[3-(methylsulfinyl)propoxy]-1'H-spiro[cyclohexane-1,4'-quinazolin]-2'(3'H)-one;

8'-fluoro-5'-([methylsulfinyl]methoxy)-1'H-spiro[cyclohexane-1,4'-quinazolin]-2'(3'H)-one, and, 8'-fluoro-5'-(2-{[1-(1H-pyrazol-3-ylmethyl)azetidin-3-yl]oxy} 1'H-spiro[cyclohexane-1,4'-quinazolin]-2'(3'H)-one.

In the following and in the foregoing text:

The term "linear or branched $(C_1-C_6)$alkylene group" represent a carbon atom chain, linear or branched containing from 1 to 6 carbon atoms. Exemples of such $(C_1-C_6)$alkylene are methylene, ethylene, isopropylene, tert-butylene and the like.

The term "$(C_1-C_6)$alkyl" represent a linear or branched carbon atom chain containing from 1 to 6 carbon atoms. Example of "$(C_1-C_6)$alkyl" are methyl, ethyl, propyl, butyl, isopropyl, tert-butyl and the like.

Examples of "saturated 4 to 6-membered heterocycle comprising one or two heteroatoms selected from nitrogen or oxygen" are azetidine, pyrrolidine, piperidine, tetrahydrofurane, tetrahydropyrane, morpholine and piperazine.

A preferred "saturated 4 to 6-membered heterocycle comprising a nitrogen atom or an oxygen atom" is azetidine.

Examples of "4 to 8-membered, aromatic or non aromatic, heterocycle comprising 1 to 4 heteroatoms selected from O, S, S(=O), $SO_2$ and N" are isoxazolyl, oxazolyl, thiazolyl, isothiazolyl, triazolyl, oxadiazolyl, thiadiazolyl, pyridyl, pyrazolyl, imidazolyl, azetidine, pyrrolidine, piperidine, tetrahydrofurane, tetrahydropyrane, morpholine and piperazine.

Preferably, said heterocycle is 5 or 6-membered, aromatic, and comprises 1 or 2 nitrogen atoms. Examples of such groups are pyridyl, pyrazolyl and imidazolyl.

The compounds utilized in the invention include pharmaceutically acceptable derivatives of compounds of formula (I) such as solvates, hydrates, pharmaceutically acceptable salts and polymorphs (different crystalline lattice descriptors). Pharmaceutically acceptable salts of a compound of formula (I) include salts having a basic part and salts having an acidic part.

The expression pharmaceutically acceptable salt of a compound of formula (I) having a basic part should be understood to refer to the addition salts of the compounds of formula (I) which may be formed from non-toxic inorganic or organic acids such as, for example, hydrobromic, hydrochloric, sulfuric, phosphoric, nitric, acetic, succinic, tartaric, citric, maleic, hydroxymaleic, benzoic, fumaric and toluenesulfonic acid salts, and the like. The various quaternary ammonium salts of the derivatives (I) are also included in this category of compounds of the invention. In addition, the expression pharmaceutically acceptable salt of a compound of formula (I) having an acidic part is understood to refer to the usual salts of the compounds of formula (I) which may be formed from non-toxic inorganic or organic bases such as, for example, the hydroxides of alkali metals and alkaline-earth metals (sodium, potassium, magnesium and calcium), amines (dibenzylethylenediamine, trimethylamine, piperidine, pyrrolidine, benzylamine and the like) or alternatively quaternary ammonium hydroxides such as tetramethylammonium hydroxide. (See also "Pharmaceutical salts" by Berge S. M. et al. (1997) *J. Pharm. Sci.* 66: 1-19, which is incorporated herein by reference.).

Use of a prodrug of a compound of the invention such as it would occur to one skilled in the art (see Bundgaard, et al., *Acta Pharm. Suec.*, 1987; 24: 233-246), is also contemplated.

General Process for the Preparation of Compounds of the Invention

The invention also relates to a process for preparing the above compounds of formula (I), said process comprising the following steps:

(1) reacting a compound 1a of formula

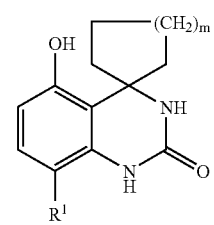

(1a)

wherein $R^1$ and m are as defined above, with a compound of formula $R^2$-LG wherein $R^2$ is as defined in the summary of the invention and LG is a leaving group such as chloride, bromide, iodide, triflate, mesylate, tosylate or nosylate, in the presence of a base, to give a compound of formula (I)

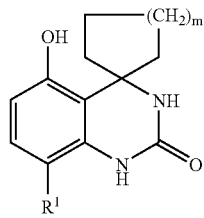
(1a)

wherein R¹, R² and m are as defined above;
(2) isolating said compound of formula (I).

Pharmaceutical Compositions

The products of the invention are administered in the form of compositions, which are appropriate for the nature, and severity of the complaint to be treated. The daily dose in humans is usually between 1 mg and 1 g of product, which may be taken in one or more individual doses. The compositions are prepared in forms which are compatible with the intended route of administration, such as, for example, tablets, coated tablets, capsules, mouthwashes, aerosols, powders for inhalation, suppositories, enemas, foams (such as rectal foams) gels or suspensions. These compositions are prepared by methods which are familiar to those skilled in the art and comprise from 0.5 to 60% by weight of active principle (compound of the invention) and 40 to 99.5% by weight of a pharmaceutical vehicle or carrier which is appropriate and compatible with the active principle and the physical form of the intended composition.

Solid form preparations include powders, tablets, dispersible granules, capsules, cachets, and suppositories. A solid carrier can be one or more substances which may also act as diluents, flavouring agents, solubilizers, lubricants, suspending agents, binders, or tablet disintegrating agents; it can also be an encapsulating material. In powders, the carrier is a finely divided solid, which is in a mixture with the finely divided active component. In tablets, the active component is mixed with the carrier having the necessary binding properties in suitable proportions and compacted in the shape and size desired. The powders, tablets, cachets or encapsulated forms for capsules preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Tablets, powders, cachets, and capsules can be used as solid dosage forms suitable for oral administration. The drug may be delivered as a spray (either in a pressurized container fitted with an appropriate valve or in a non-pressurized container fitted with a metering valve).

Liquid form preparations include solutions, suspensions, and emulsions.

Sterile water or water-propylene glycol solutions of the active compounds may be mentioned as an example of liquid preparations suitable for parenteral administration.

Liquid preparations can also be formulated in solution in aqueous polyethylene glycol solution.

Aqueous solutions for oral administration can be prepared by dissolving the active component in water and adding suitable colorants, flavouring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify. Enemas are obtained according to known procedures to prepare solutions adapted for rectal administration. Foams are prepared according to known methods (these foams can notably be similar to those used to administer a drug such as 5-ASA for treating rectocolite).

Preferably the pharmaceutical preparation is in unit dosage form. In such form, the preparation is divided into unit doses containing appropriate quantities of drug. The unit dosage form can be a packaged preparation, the package containing discrete quantities of the preparation, for example, packaged tablets, capsules, and powders in vials or ampoules. The unit dosage form can also be a capsule, cachet, or tablet itself, or it can be the appropriate number of any of these packaged forms.

Use

The compounds of the invention are PDE inhibitors, and particularly PDE7 inhibitors. These compounds have low $IC_{50}$ values, typically at most 5 μM, preferably below 1 μM, and even below 100 nM.

It has been shown according to the invention that compounds of the invention are selective PDE7 inhibitors. "selective PDE7 inhibitors" refers to a compound which have an $IC_{50}$ for PDE7 at least 5 times lower than the $IC_{50}$ for a PDE distinct from PDE7, and preferably at least 10 times, 15 times, 20 times, 30 times, 40 times, 50 times or 100 times lower than the $IC_{50}$ value for a PDE distinct from PDE7.

A PDE distinct from PDE7 refers preferably to a PDE chosen from PDE1, PDE3, PDE4 or PDE5.

In particular, it has been shown according to the invention that the compounds of the invention, and more particularly the family of compounds given as examples in the present description, have an $IC_{50}$ value for the enzyme PDE7 which is often 100 times lower than the value of their $IC_{50}$ for a PDE distinct from PDE7, in particular PDE1, PDE3, PDE4 or PDE5.

Compounds of the invention can be used in the treatment of various diseases, as they can modulate inflammatory and immunological processes due to the increase of intracellular cAMP levels.

Examples of diseases that can be treated include T and B-cell-related diseases, autoimmune diseases, osteoarthritis, rheumatoid arthritis, multiple sclerosis, osteoporosis, chronic obstructive pulmonary disease (COPD), asthma, cancer such as leukemia, acquired immune deficiency syndrome (AIDS), allergy, inflammatory bowel disease (IBD), ulcerative colitis, Crohn's disease, pancreatitis, dermatoses such as psoriasis and atopic dermatitis, glomerulonephritis, conjunctivitis, autoimmune diabete, graft rejection, epilepsy, muscular atrophy or systemic lupus erythematosus. Compounds of the invention are particularly useful for the treatment of asthma, allergy, atopic dermatitis, osteoporosis and cancer such as leukemia.

Processes for Synthesizing Compounds of the Invention

Scheme 1

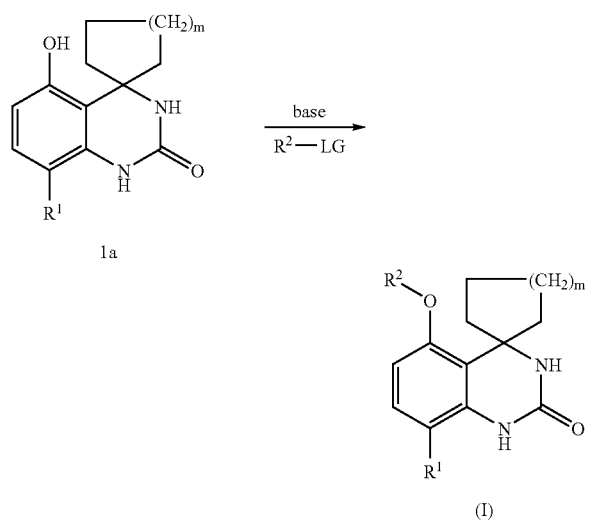

In scheme 1, $R^1$, $R^2$ and m are as defined in the summary of the invention and LG is a leaving group such as chloride, bromide, iodide, triflate, mesylate, tosylate or nosylate.

Compound 1a can be prepared using processes disclosed in PCT/EP02/03594.

Compound 1a is reacted with $R^2$-LG in presence of a base in a suitable solvent to yield the O-substituted quinazolinone. Various solvents, operating conditions and bases can be used and will be easily determined by the skilled person. For example, and without any limitation, one can use potassium carbonate, cesium carbonate or sodium hydride as base in dimethylformamide as solvent.

SYNTHESIS EXAMPLES

Preparation of Intermediates

Preparation of Intermediate a

8'-chloro-5'-([methylthio]methoxy)-1'H-spiro[cyclo-hexane-1,4'-quinazolin]-2'(3'H)-one To a solution of 8'-chloro-5'-hydroxy-1'H-spiro[cyclohex-ane-1,4'-quinazolin]-2'(3'H)-one, which can be prepared according to processes disclosed in example 63 of PCT/EP02/03594 (6 g, 2.25 mmol) in dimethylformamide (6 mL) was added potassium carbonate (0.776 g, 5.6 mmol) and chloromethyl methyl sulfide (0.26 mL, 2.7 mmol). The mixture was stirred in a sealed tube at 100° C. for 3 days. Dimethylformamide was removed by evaporation in vacuo. Water was added to the residue and the aqueous layer was extracted twice with ethyl acetate.

The combined ethyl acetate layers were dried over sodium sulfate, filtered and concentrated in vacuo. The crude compound was purified by column chromatography on silica gel (fixed with heptane and eluted with methanol 0.5% to 2% in dichloromethane) to afford intermediate a as a solid (0.3 g, 41%).

Purity=93.45% $^1$H NMR [$(CD_3)_2SO$] δ 7.95 (br s, 1H, NH), 7.26 (d, J=8.8 Hz, 1H, CH), 7.02 (br s, 1H, NH), 6.69 (d, J=9.1 Hz, 1H, CH), 5.30 (s, 2H, $CH_2$), 2.47-2.54 (m, 2H), 2.25 (s, 3H, $CH_3$), 1.70-1.87 (m, 2H), 1.56-1.67 (m, 3H), 1.40-1.54 (m, 2H), 1.21-1.30 (m, 1H).

Preparation of Intermediate b

8'-chloro-5'-(2-iodoethoxy)-1'H-spiro[cyclohexane-1,4'-quinazolin]-2'(3'H)-one

To a solution of the 8'-chloro-5'-(2-hydroxyethoxy)-1'H-spiro[cyclohexane-1,4'-quinazolin]-2'(3'H)-one, which can be prepared according to processes disclosed in example 78 of PCT/EP02/03594, (0.6 g, 1.93 mmol) in anhydrous dimethylformamide (15 mL), iodine (2.9 g, 11.4 mmol) and triphenylphosphine (3 g, 11.4 mmol) were added under nitrogen atmosphere. The mixture was stirred at room temperature for one day in the dark. The dimethylformamide was then removed by evaporation and the residue was partitioned between dichloromethane and a satured solution of $Na_2S_2O_4$. The organic layer was dried over sodium sulfate, filtered, and concentrated under reduced pressure to give the intermediate b.

Preparation of Intermediate c

8'-fluoro-5'-hydroxy-1'H-spiro[cyclohexane-1,4'-quinazolin]-2'(3'H)-one

To a stirred solution of 2,6-dibromo-4-fluorophenol (214.5 g, 0.794 mol) in acetone (4.3 L), potassium carbonate (120.6 g, 0.874 mol) and methyl iodide (54.4 mL, 0.874 mol) were added at room temperature. The mixture was heated to reflux for 1.5 hours cooled to 25° C. and filtered, washing the filter cake with dichloromethane (2×1.5 L). The filtrate was concentrated in vacuo at 40° C. The crude product was slurred in dichloromethane (1 L) for 30 minutes at 25° C., filtered and concentrated in vacuo at 40° C. to give 1,3-Dibromo-5-fluoro-2-methoxybenzene as an off-white crystalline solid (223.3 g, 98.9%).

$^1$H NMR [$(CD_3)_2SO$] δ 7.71 (d, J=8.1 Hz, 2H), 3.80 (s, 3H).

To a stirred solution of c.$H_2SO_4$ (740 mL) at 0 to 5° C. was added 1,3-dibromo-5-fluoro-2-methoxybenzene (223.3 g, 0.786 mol). A solution of fuming nitric acid (90%, 38 mL, 0.815 mol) in c.$H_2SO_4$ (740 mL) was added dropwise, maintaining the temperature between 0 and 5° C. The reaction mixture was stirred at 3 to 5° C. for 2 hours, quenched into ice (2.2 kg) and extracted with dichloromethane (3×2 L). The combined dichloromethane extracts were washed with saturated aqueous $NaHCO_3$ solution (2×2 L), dried over $Na_2SO_4$, filtered and the filter cake washed with DCM (3×400 mL). The filtrate was concentrated in vacuo at 40° C. to give 1,3-Dibromo-5-fluoro-2-methoxy-4-nitrobenzene as a pale orange crystalline solid (244.9 g, 95%).

$^1$H NMR [$(CD_3)_2SO$] δ 8.25 (d, J=9.4 Hz, 1H), 3.85 (s, 3H).

A 2.0 L pressure reactor was charged with 10% Pd/C (50% wet paste, 10 g). A solution of 1,5-dibromo-3-fluoro-6-methoxy-5-nitrobenzene (50 g, 0.152 mol) in ethanol (absolute grade, 1.5 L) was added to the catalyst under $N_2$. The stirred reaction mixture was subjected to three cycles of vacuum followed by $N_2$ purge. The reaction mixture was evacuated prior to the introduction of $H_2$ at a pressure of 4 bars. The reaction mixture was evacuated and $H_2$ was introduced until a pressure of 7 bars was reached. The reaction mixture was stirred at 25° C. for 48 hours, with periodic injections of $H_2$ to maintain the internal pressure at 7 bars (note that after 24 hours, the catalyst was replaced). After the reaction had reached completion, the catalyst was removed by filtration through 2 glass microfibre pads under an atmosphere of $N_2$ and the filtrate was concentrated to dryness under reduced pressure at 45° C. The resulting dark orange solid was dissolved in water (500 mL) and the pH of the resulting solution adjusted to >12 using aqueous NaOH (1N, 400 mL). The resulting brown suspension was extracted with tert-butylmethylether (2×1 L). The combined organic extracts were washed with water (500 mL), dried over sodium sulfate, filtered and concentrated in vacuo at 40° C. to afford 2-Fluoro-5-methoxyaniline (18.0 g, 84%) as a brown solid.

$^1$H NMR [(CD$_3$)$_2$SO] δ 6.87 (dd, J=11.1, 8.7 Hz, 1H), 6.33 (dd, J=7.7, 3.2 Hz, 1H), 6.05 (dt, J=8.7, 3.2 Hz, 1H), 5.11 (br s, 2H), 3.65 (s, OCH$_3$, 3H); MS (ES) m/z 183 (M+CH$_3$CN+H)$^+$.

To a stirred solution of 2-fluoro-5-methoxyaniline (35.15 g, 249 mmol) in acetic acid (99 mL) and water (177 mL) at 35° C. was added potassium cyanate (40 g, 0.49 mol) in water (170 mL) over 20 minutes under $N_2$. The mixture was stirred at 40° C. for 20 min and at 18 to 20° C. for 2 h, and then quenched into water (500 mL). The crude product was filtered, washed with water (1.2 L), heptane (50 mL) and slurried in a mixture of tert-butylmethylether (100 mL) and ethyl acetate (5 mL) for 5 minutes at ambient temperature. The product was filtered, washed with tert-butylmethylether (30 mL) and dried in vacuo at 40° C. to give N-(2-Fluoro-5-methoxyphenyl)urea (31.75 g, 69%) as a light-brown solid.

$^1$H NMR [(CD$_3$)$_2$SO] δ 8.19 (br s, 1H), 7.67 (dd, 1H), 6.95 (dd, 1H), 6.31 (dd, 1H), 6.08 (br s, 2H), 3.55 (s, 3H).

To a stirred solution of polyphosphoric acid (20 g) at 100° C. was added N-(2-fluoro-5-methoxyphenyl)urea (900 mg, 4.89 mmol) over 5 minutes followed by cyclohexanone (719 mg, 7.33 mmol) in one portion under $N_2$. The mixture was stirred at 100° C. for 2 hours, cooled to 35° C. and quenched into water (400 mL). The crude product was filtered and washed with water (100 mL). The isolated solid was slurried in a mixture of tert-butylmethylether (8 mL) and ethyl acetate (4 mL) at 50° C. for 10 minutes, filtered, washed with tert-butylmethylether (10 mL) and dried in vacuo at 40° C. to give 8'-fluoro-5'-methoxy-1'H-spiro[cyclohexane-1,4'-quinazolin]-2'(3'H)-one (900 mg, 70%) as a light-brown solid, purity (97.3%).

$^1$H NMR [(CD$_3$)$_2$SO] δ 8.92 (br s, 1H), 7.04 (app. t, J=9.5 Hz, 1H), 6.86 (br s, 1H), 6.54 (dd, J=9.1, 4.2 Hz, 1H), 3.76 (s, 3H), 2.36-2.44 (ddd, J=13.5, 13.5, 4.4 Hz, 2H), 1.72-1.86 (m, 2H), 1.52-1.65 (m, 3H), 1.40-1.50 (m, 2H), 1.12-1.24 (m, 1H); $^{13}$C NMR [(CD$_3$)$_2$SO] δ 153.39, 153.37, 151.65, 145.75, 143.15, 126.87, 126.71, 116.3, 114.78, 114.57, 105.37, 105.29, 57.95, 56.77, 36.24, 25.45, 20.49; MS (ES+) m/z 265.1 (M+H)$^+$.

To a stirred solution of 8'-fluoro-5'-methoxy-1'H-spiro[cyclohexane-1,4'-quinazolin]-2'(3'H)-one (2.34 g, 8.84 mmol) in DCM (250 mL) at 0 to 5° C. was added boron tribromide (11.07 g, 44.2 mmol) dropwise over 20 minutes under $N_2$. The mixture was stirred at 5° C. for 10 mins and gradually allowed to warm up to ambient temperature. Stirring was continued at ambient temperature for 18 h and a further portion of BBr$_3$ (5 g, 20 mmol) was added. The mixture was left to stir for a further 24 hours and quenched with saturated NaHCO$_3$ solution (500 mL) at 10° C. over 30 minutes. The mixture was stirred at ambient temperature for 1 hour and the aqueous layer was separated from dichloromethane and extracted with ethyl acetate (2×500 mL). The organic layers were washed with saturated NaHCO$_3$ solution (200 mL), water (300 mL), dried over anhydrous MgSO$_4$, filtered and concentrated in vacuo at 40° C. to give the crude product. The crude material was slurred in tert-butylmethylether (10 mL) at 18 to 20° C. for 5 minutes, filtered and dried in vacuo at 40° C. to give 8'-fluoro-5'-hydroxy-1'H-spiro[cyclohexane-1,4'-quinazolin]-2'(3'H)-one (1.5 g, 68%) as a light-brown solid, purity (99.9%).

$^1$H NMR [(CD$_3$)$_2$SO] δ 9.60 (br s, 1H), 8.80 (br s, 1H), 6.86 (dd, J=10.0, 8.9 Hz, 1H), 6.82 (br s, 1H), 6.31 (dd, J=8.9, 4.5 Hz, 1H), 2.50-2.60 (m, 2H), 1.71-1.85 (m, 2H), 1.50-1.64 (m, 3H), 1.40-1.50 (m, 2H) and 1.10-1.23 (m, 1H); MS (ES+) m/z 251.1 (M+H)$^+$.

Preparation of Intermediate d 3-(methylthio)propyl methanesulfonate

To a solution of 3-methylthio-1-propanol (2 mL, 19.4 mmol) in dichloromethane (50 mL) and triethylamine (3.2 mL, 23.28 mmol) at 0° C. was added dropwise methane sulfonyl chloride (1.8 mL, 23.28 mmol) under a nitrogen atmosphere. The mixture was stirred and allowed to warm up to room temperature over one hour and stirred at room temperature for 2.5 hours. The dichloromethane was removed under reduced pressure to give the crude intermediate d.

Preparation of Intermediate e

8'-fluoro-5'-[3-(methylthio)propoxy]-1'H-spiro[cyclohexane-1,4'-quinazolin]-2'(3'H)-one To a solution of intermediate c (0.5 g, 2 mmol) in anhydrous dimethylformamide (4 mL) was added potassium carbonate (0.331 g, 2.4 mmol) and intermediate d (2.4 mmol). The mixture was stirred in a sealed tube at 100° C. for 21.5 hours. Potassium carbonate (0.331 g, 2.4 mmol) and intermediate d (2.4 mmol) were added and the mixture was stirred at 100° C. for 3 days. The dimethylformamide was evaporated and the residue was partitioned between dichloromethane and water. The aqueous layer was extracted twice with dichloromethane, dried over sodium sulfate, filtered and concentrated under reduced pressure. The residue was purified through a cake of silica gel eluting with a gradient of dichloromethane containing from 0 to 3% of methanol. The residue was triturated in ethyl ether, filtered and dried under vaccum to give the intermediate e (0.22 g, 32.5%)

$^1$H NMR [(CD$_3$)$_2$SO] δ 8.85 (br s, 1H, NH), 7.01 (dd, J=10.1, 9.1 Hz, 1H, CH), 6.83 (br s, 1H, NH), 6.52 (dd, J=9.1, 4.1 Hz, 1H, CH), 4.03 (t, J=6.0 Hz, 2H, CH$_2$), 2.67 (t, J=7.3 Hz, 2H, CH$_2$), 2.40-2.55 (m, 2H), 2.07 (s, 3H, CH$_3$), 1.98-2.07 (m, 2H), 1.73-1.87 (m, 2H), 1.54-1.69 (m, 3H), 1.40-1.51 (m, 2H), 1.10-1.25 (m, 1H).

Preparation of Intermediate f

8'-fluoro-5'-([methylthio]methoxy)-1'H-spiro[cyclohexane-1,4'-quinazolin]-2'(3'H)-one To a solution of intermediate c (0.6 g, 2.4 mmol) in anhydrous dimethylformamide (6 mL) were added potassium carbonate (0.795 g, 6 mmol) and chloromethyl methylsulfide (0.242 mL, 2.8 mmol). The mixture was stirred in a sealed tube at 100° C. for 28 hours. Additional chloromethyl methylsulfide (0.242 mL, 2.8 mmol) was added in the mixture and stirred at 100° C. for 24 hours. The dimethylformamide was evaporated and the residue was partitioned between dichloromethane and water. The aqueous layer was extracted twice with dichloromethane, dried over sodium sulfate, filtered and the mixture was concentrated under reduced pressure. The residue was purified through a cake of silica gel, eluting with a gradient of dichloromethane containing from 0 to 3% of methanol to give the intermediate f (0.5 g, 81%)

$^1$H NMR [(CD$_3$)$_2$SO] δ 8.95 (br s, 1H, NH), 7.05 (t, 1H, CH), 6.86 (br s, 1H, NH), 6.56 (dd, 1H, CH), 5.28 (s, 2H, CH$_2$), 2.40-2.50 (m, 2H), 2.25 (s, 3H, CH$_3$), 1.70-1.88 (m, 2H), 1.55-1.68 (m, 3H), 1.38-1.55 (m, 2H), 1.10-1.29 (m, 1H).

Preparation of Intermediate g

5'-[(1-benzhydrylazetidin-3-yl)oxy]-8'-fluoro-1'H-spiro[cyclohexane-1,4'-quinazolin]-2'(3'H)-one To a solution of intermediate c (3.15 g, 12.58 mmol) in anhydrous dimethylformamide (25 mL) were added 1-benzhydrylazetidin-3-yl methanesulfonate (8 g, 25.17 mmol) and potassium carbonate (7 g, 50.34 mmol). The mixture was stirred at 100° C. for 48 hours, under argon. The dimethylformamide was evaporated and the residue was partitioned between dichloromethane and water. The aqueous layer was extracted twice with ethyl acetate, dried over sodium sulfate, filtered and concentrated under reduced pressure. The crude compound was purified by column chromatography (silica gel eluting with 0% to 1% methanol in dichloromethane) to afford the intermediate g (3 g, 50%).

$^1$H NMR [CDCl$_3$] δ 7.34-7.45 (m, 4H), 7.12-7.32 (m, 6H), 6.76-6.86 (m, 2H, NH and CH), 6.08 (dd, 1H, CH), 5.51 (br s, 1H, NH), 4.78 (m, 1H, CH), 4.40 (s, 1H, CH), 3.70 (m, 2H, CH$_2$), 3.09 (m, 2H, CH$_2$), 2.50-2.60 (m, 2H), 1.63-1.86 (m, 5H), 1.45-1.60 (m, 2H), 1.18-1.34 (m, 1H).

Preparation of intermediate h

5'-(azetidin-3-yloxy)-8'-fluoro-1'H-spiro[cyclohexane-1,4'-quinazolin]-2'(3'H)-one To a solution of intermediate g (1.86 g, 3.94 mmol) in anhydrous methanol (50 mL) was added Pd(OH)$_2$ at 20% (0.634 g). Vacuum was applied to the mixture and hydrogen was added. The mixture was stirred for 2 days and then filtered through a cake of celite using methanol as eluent. The filtrate was concentrated under reduced pressure. The residue was triturated in dichloromethane, filtered and dried under vaccum to give the intermediate h (0.95 g, 78.8%)

$^1$H NMR [(CD$_3$)$_2$SO] δ 8.88 (br s, 1H, NH), 6.98 (dd, J=9.1, 9.1 Hz, 1H, CH), 6.85 (br s, 1H, NH), 6.72 (dd, J=9.1, 4.0 Hz, 1H, CH), 4.95 (m, 1H, CH), 3.74-3.84 (m, 2H, CH$_2$), 3.47-3.57 (m, 2H, CH$_2$), 2.52-2.59 (m, 2H), 1.72-1.87 (m, 2H), 1.54-1.69 (m, 3H), 1.42-1.53 (m, 2H), 1.10-1.27 (m, 1H).

PREPARATION OF EXAMPLES

Example 1

5'-(2-[(2-amino-2-oxoethyl)amino]ethoxy)-8'-chloro-1'H-spiro[cyclohexane-1,4'-quinazolin]-2'(3'H)-one $R^1$=Cl, $R^2$=—CH$_2$—CH$_2$—NH—CH$_2$—CO—NH$_2$, m=2.  Formula (I)

To a stirred suspension of 8'-chloro-5'-(2-[(2-methoxy-2-oxoethyl)amino]ethoxy)-1'H-spiro[cyclohexane-1,4'-quinazolin]-2'(3'H)-one, which can be prepared according to processes disclosed example 98 of in PCT/EP02/03594, (1.0 g, 2.52 mmol) in ethanol (20 mL) at room temperature, was added concentrated aqueous ammonia (30 mL, 580 mmol). The resulting mixture was stirred at 60° C. for 2.25 hours. A further aliquot of concentrated aqueous ammonia (15 mL, 290 mmol) was added and the mixture was stirred at 60° C. for 3.75 hours. The solution was evaporated under vacuum at 45° C. and azeotroped dry with ethanol (40 mL) to afford an off-white solid residue. The crude product was purified by column chromatography (silica gel 50 g, eluting with 10% methanol in dichloromethane) to yield the title compound (0.35 g, 4.5 mmol, 37.8%) as a white solid after drying in vacuo at 50° C. (purity 99.5%).

$^1$H NMR [(CD$_3$)$_2$SO] δ 7.98 (br s, 1H, NH), 7.29 (br s, 1H, NH), 7.26 (d, J=9.0 Hz, 1H), 7.08 (br s, 1H, NH), 7.03 (br s, 1H, NH), 6.64 (d, J=9.0 Hz, 1H), 4.02 (t, J=5.5 Hz, 2H), 3.12 (s, 2H), 2.90 (t, J=5.5 Hz, 2H), 2.52 (m, 2H), 2.27 (br s, 1H, NH), 1.72-1.83 (m, 2H), 1.55-1.60 (m, 3H), 1.44-1.48 (m, 2H), 1.21 (m, 1H); $^{13}$C NMR (CDCl$_3$) δ 174.12, 155.56, 151.35, 134.58, 129.38, 116.32, 110.78, 107.93, 69.03, 58.14, 52.69, 49.01, 36.18, 25.45, 20.59; MS (LC-MS) m/z 369.2 (M$^{37}$Cl+H)$^+$, 367.2 (M$^{35}$Cl+H)$^+$.

Example 2

8'-chloro-5'-([methylsulfinyl]methoxy)-1'H-spiro[cyclohexane-1,4'-quinazolin]-2'(3'H)-one $R^1$=Cl, $R^2$=CH$_2$—SO—CH$_3$, m=2  Formula (I)

To a solution of intermediate a (0.3 g, 0.92 mmol) in methanol (20 mL) and water (5 mL) at 0° C. was added oxone (0.368 g, 0.6 mmol) and NaHCO$_3$ (0.302 mg, 3.59 mmol). The mixture was stirred for 1 hour at 0° C. and 1 hour at room temperature and then concentrated under reduced pressure. The residue was taken into dichloromethane and water. The organic layer was partitioned and the aqueous layer was extracted twice with dichloromethane. The combined organic layers were dried over sodium sulfate, filtered and reduced under pressure vacuum. The residue was purified by column chromatography on silica gel (10 g) with 1% to 2% methanol in dichloromethane to afford the title compound (0.13 g, 41%)

Purity=98.8%

$^1$H NMR [(CD$_3$)$_2$SO] δ 8.08 (br s, 1H, NH), 7.31 (d, J=9.0 Hz, 1H, CH), 7.06 (br s, 1H, NH), 6.82 (d, J=9.0 Hz, 1H, CH), 5.29 (d, J=10.35 Hz, 1H, CH$_2$), 5.07 (d, J=10.35 Hz, 1H, CH$_2$), 2.65 (s, 3H, CH$_3$), 2.42-2.54 (m, 2H), 1.72-1.87 (m, 2H), 1.56-1.67 (m, 3H), 1.40-1.54 (m, 2H), 1.20-1.32 (m, 1H)

Example 3

5'-(2-{[2-(acetylamino)ethyl]amino}ethoxy)-8'-chloro-1'H-spiro[cyclohexane-1,4'-quinazolin]-2'(3'H)-one $R^1$=Cl, $R^2$=CH$_2$—CH$_2$—NH—CH$_2$—CH$_2$—NH—CO—CH$_3$, m=2.  Formula (I)

To a solution of intermediate b (0.276 mmol) in ethanol (3 mL) were added triethylamine (0.15 mL, 1.08 mmol) and N-acetylethylenediamine (0.033 g, 0.323 mmol). The mixture was stirred in a sealed tube at 70° C. for 2 days. The ethanol was removed by evaporation and the residue was partitioned between ethyl acetate and an aqueous solution of hydrochloric acid. The aqueous layer was washed with ethyl acetate, basified with a solution of sodium hydroxide and extracted with dichloromethane. The organic layer was dried over sodium sulfate, filtered and concentrated under reduced pressure. The crude compound was purified by column chromatography (silica 5 g eluting with 2% to 5% methanol (with 1% ammonia) in dichloromethane). The compound was washed with diethyl ether, filtered and dried under vaccum to give the title product (8 mg, 9% two steps).

Purity=98.95% $^1$H NMR [(CD$_3$)$_2$SO] δ 7.92 (br s, 1H, NH), 7.79 (br s, 1H, NH), 7.24 (d, J=9.2 Hz, 1H, CH), 7.00 (br s, 1H, NH), 6.63 (d, J=8.8 Hz, 1H, CH), 4.01 (t, J=5.5 Hz, 2H, CH$_2$), 3.10 (q, J=6.0 Hz, 2H, CH$_2$), 2.92 (t, J=4.4 Hz, 2H, CH$_2$), 2.60 (m, 2H, CH$_2$), 1.75 (s, 3H, CH$_3$), 1.71-1.83 (m, 3H), 1.58-1.67 (m, 3H), 1.40-1.58 (m, 3H), 1.18-1.15 (m, 1H).

Example 4

8'-fluoro-5'-[3-(methylsulfinyl)propoxy]-1'H-spiro[cyclohexane-1,4'-quinazolin]-2'(3'H)-one $R^1$=F, $R^2$=CH$_2$—CH$_2$—CH$_2$—SO—CH$_3$, m=2          Formula (I)

To a solution of intermediate e (0.1 g, 0.29 mmol) in methanol (10 mL) and water (2.5 mL) at 0° C., were added oxone (0.118 g, 0.192 mmol) and NaHCO$_3$ (0.097 g, 1.152 mmol). The mixture was stirred for 3 hours and was allowed to warm up to room temperature over 2 hours. The methanol was evaporated and the residue was partitioned between dichloromethane and water. The aqueous layer was extracted twice with dichloromethane, dried over sodium sulfate, filtered and concentrated under reduced pressure. The residue was purified by column chromatography (silica gel 5 g, eluting with 1% to 2% methanol (with 1% ammonia) in dichloromethane) to afford the title compound (0.025 g, 24%).

Purity=95.19% $^1$H NMR [(CD$_3$)$_2$SO] δ 8.86 (br s, 1H, NH), 7.03 (dd, J=8, 8 Hz, 1H, CH), 6.82 (br s, 1H, NH), 6.52 (dd, J=8, 4 Hz, 1H, CH), 4.07 (t, J=6 Hz, 2H, CH$_2$), 2.88-2.97 (m, 1H, CH$_2$), 2.77-2.86 (m, 1H, CH$_2$), 2.56 (s, 3H, CH$_3$), 2.40-2.51 (m, 2H), 2.13 (m, 2H), 1.72-1.86 (m, 2H), 1.56-1.66 (m, 3H), 1.42-1.52 (m, 2H), 1.12-1.25 (m, 1H).

Example 5

8'-fluoro-5'-([methylsulfinyl]methoxy)-1'H-spiro[cyclohexane-1,4'-quinazolin]-2'(3'H)-one $R^1$=F, $R^2$=CH$_2$—SO—CH$_3$, m=2          Formula (I)

To a solution of intermediate e (0.5 g, 1.6 mmol) in methanol (25 mL) and water (7 mL) at 0° C. were added oxone (0.644 g, 1 mmol) and NaHCO$_3$ (0.528 g, 6.28 mmol) and the mixture was stirred for 1.25 hours. The mixture was allowed to warm up to room temperature over 3.5 hours. The methanol was evaporated and the residue was partitioned between dichloromethane and water. The aqueous layer was extracted twice with dichloromethane, dried over sodium sulfate, filtered and concentrated under reduced pressure. The crude material was purified by a first column chromatography (silica gel 10 g, eluting with 1% methanol (with 1% ammonia) in dichloromethane) and followed by a second column chromatography (silica gel 10 g, eluting with 1% to 5% methanol in dichloromethane) to afford the title compound (0.090 g, 17%).

Purity=100% $^1$H NMR [(CD$_3$)$_2$SO] δ 8.98 (br s, 1H, NH), 7.08 (dd, J=9.6, 9.6 Hz, 1H, CH), 6.86 (br s, 1H, NH), 6.72 (dd, J=9.1, 4.8 Hz, 1H, CH), 5.26 (d, J=10.1 Hz, 1H, CH$_2$), 5.03 (d, J=10.7 Hz, 1H, CH$_2$), 2.64 (s, 3H, CH$_3$), 2.40-2.48 (m, 2H), 1.72-1.86 (m, 2H), 1.54-1.66 (m, 3H), 1.41-1.51 (m, 2H), 1.17-1.31 (m, 1H)

Example 6

8'-fluoro-5'-(2-{[1-(1H-pyrazol-3-ylmethyl)azetidin-3-yl]oxy}1'H-spiro[cyclohexane-1,4'-quinazolin]-2'(3'H)-one $R^1$=F, $R^2$=azetidine-CH$_2$-3-pyrazole, m=2          Formula (I)

To a suspension of intermediate h (0.4 g, 1.31 mmol) in 1,2-dichloroethane (8 mL), triethylamine (0.364 mL, 2.62 mmol) and glacial acetic acid (0.15 mL, 2.62 mmol) at 0° C. was added pyrazol-3-carboxyaldehyde (0.378 g, 3.93 mmol). The resulting mixture was stirred for 5 minutes, then cooled to 0° C., before addition of sodium triacetoxyborohydride (1.378 g, 5.24 mmol). The mixture was stirred at room temperature for one day and basified to pH=7-8 with a saturated solution of NaHCO$_3$. The precipitate was filtered, washed with water and crystallized with dichloromethane/methanol (50/50) to give the title compound (0.12 g, 24%).

Purity=97.7% $^1$H NMR [(CD$_3$)$_2$SO] δ 12.56 (br s, 1H, NH), 8.87 (br s, 1H, NH), 7.62 (br s, 1H, NH), 6.96 (dd, J=9.6, 9.6 Hz, 1H, CH), 6.83 (br s, 1H, NH), 6.24 (dd, J=4, 4 Hz, 1H, CH), 6.12 (d, J=2.2 Hz, 1H, CH), 4.76 (m, 1H, CH), 3.69 (t, J=6.6 Hz, 2H, CH$_2$), 3.60 (s, 2H, CH$_2$), 3.04 (t, J=6.6 Hz, 2H, CH$_2$), 2.36-2.48 (m, 2H), 1.69-1.86 (m, 2H), 1.59-1.68 (m, 1H), 1.51-1.59 (m, 2H), 1.42-1.51 (m, 2H), 1.05-1.22 (m, 1H)

BIOLOGICAL RESULTS

The capacity of the compounds of the invention to inhibit cyclic nucleotide phosphodiesterases was evaluated by measuring their IC$_{50}$ (concentration necessary to inhibit the enzymatic activity by 50%).

PDE1C, PDE3A, PDE4B2, PDE7A1, PDE7B and PDE11A were cloned and expressed in insect cells Sf21 using the baculovirus expression system and the cell culture supernatant was used directly as enzyme source.

Measurement of the enzymatic activity for the various types of PDE was then made according to a method adapted from W. J. Thompson et al. 1979, Advances in Cyclic Nucleotide Research, Vol. 10: 69-92, ed. G. Brooker et al. Raven Press, NY.

The substrate used was tritiated cGMP (16 Ci/mmol) for PDE1 and PDE11 and tritiated cAMP (35 Ci/mmol) for PDE3, PDE4 and PDE7. The substrate concentration was 28 nM for PDE1, PDE11 and 13 nM for PDE3, PDE4 and PDE7. The enzymatic reaction was stopped after 30 min by addition of SPA yttrium silicate beads (Amersham).

The IC$_{50}$ (μM) were determined for examples 1 to 6 and were found to be below 1 μM.

The invention claimed is:

1. A compound of formula (I):

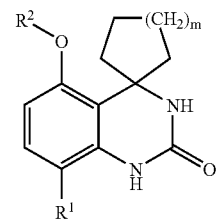

wherein
m is 1, 2 or 3;
$R^1$ is selected from CH$_3$, Cl, Br and F;

$R^1$ is selected from $CH_3$, Cl, Br and F;
$R^2$ is selected from
(a) $Q^1$-$Q^2$-$Q^3$-$Q^4$ wherein:
   $Q^1$ is a single bond or a linear or branched $(C_1$-$C_6)$ alkylene group;
   $Q^2$ is a saturated 4- to 6-membered heterocycle comprising a nitrogen atom;
   $Q^3$ is a linear $(C_1$-$C_4)$alkylene group;
   $Q^4$ is a 5 or 6-membered, aromatic heterocycle comprising 1 to 4 nitrogen atoms, said heterocycle being optionally substituted with methyl;
   the atom of $Q^2$ bound to $Q^1$ is a carbon atom; and
   the atom of $Q^4$ bound to $Q^3$ is a carbon atom;
(b) $(C_1$-$C_6)$alkyl, said alkyl group being substituted with a group selected from $OR^4$, $COOR^4$, $NR^4R^5$, $NRC(=O)R^4$, $C(=O)NR^4R^5$ and $SO_2NR^4R^5$, wherein;
R is H or $(C_1$-$C_6)$alkyl;
$R^4$ is $(C_1$-$C_6)$alkyl substituted with 1 to 3 groups selected from $S(=O)R^6$, $SO_2R^6$, $NR'C(=O)R^7$, $NR'SO_2R^6$, $C(=O)NR^7R^8$, $O$-$C(=O)NR^7R^8$ and $SO_2NR^7R^8$, wherein $R^6$ is $(C_1$-$C_6)$alkyl and R', $R^7$ and $R^8$ are the same or different and are selected from H and $(C_1$-$C_6)$alkyl; and
$R^5$ is selected from $R^4$, H and $(C_1$-$C_6)$alkyl;
(c) $(C_1$-$C_6)$alkyl, said alkyl group being:
substituted with 1 to 3 groups selected from $OC(=O)R^{4a}$, $SR^{4a}$, $S(=O)R^3$, $NR^aCOOR^{4a}$, $NR^a$-$C(=O)$-$NR^{4a}R^{5a}$, $NR^a$-$SO_2$—$NR^{4a}R^{5a}$, and $NR^a$-$SO_2$-$R^3$, and optionally substituted with OH or $OCH_3$;
wherein
$R^a$ is selected from H and $CH_3$;
$R^3$ is $(C_1$-$C_6)$alkyl, unsubstituted or substituted with 1 to 3 groups, selected from F, CN, $S(=O)R^6$, $SO_3H$, $SO_2R^6$, $C(=O)$—NH—$SO_2$-$CH_3$, $OR^7$, $SR^7$, $COOR^7$, $C(=O)R^7$, $O$—$C(=O)NR^7R^8$, $NR^7R^8$, $NR'C(=O)R^7$, $NR'SO_2R^6$, $C(=O)NR^7R^8$ and $SO_2NR^7R^8$, wherein $R^6$ is $(C_1$-$C_6)$alkyl and R', $R^7$ and $R^8$ are the same or different and are selected from H and $(C_1$-$C_6)$alkyl;
$R^{4a}$ and $R^{5a}$ are the same or different and are selected from H and $R^3$; their racemic forms, their isomers or their pharmaceutically acceptable salts.

2. A compound of claim 1 wherein:
$R^2$ is $(C_1$-$C_4)$alkyl substituted with —$NR^4R^5$ or —$C(=O)NR^4R^5$;
$R^4$ is $(C_1$-$C_6)$alkyl substituted with —$S(=O)CH_3$, —NHC$(=O)CH_3$ or —$C(=O)NR^7R^8$;
$R^5$ H or methyl; and
$R^7$ and $R^8$ are the same or different and are H or methyl.

3. A compound of claim 1 wherein:
$R^2$ is $(C_1$-$C_6)$alkyl substituted with —$S(=O)R^3$;
$R^3$ is $(C_1$-$C_6)$alkyl optionally substituted with one to three groups selected from —$S(=O)R^6$, —$SO^2R^6$, —$NR^7R^8$, —$OR^7$, —$NR'C(=O)R^7$, —$NR'SO_2R^6$;
—$C(=O)NR^7R^8$; and —O—$C(=O)NR^7R^8$; wherein
$R^6$ is $(C_1$-$C_6)$alkyl and R', $R^7$ and $R^8$ are the same or different and are H or $(C_1$-$C_6)$alkyl.

4. A compound of claim 1 wherein $R^2$ is $(C_1$-$C_6)$alkyl substituted with —$S(=O)R^3$; and $R^3$ is $(C_1$-$C_6)$alkyl.

5. A compound of claim 1 wherein:
$R^2$ is $Q^1$—$Q^2$—$Q^3$—$Q^4$;
$Q^1$ is a single bond;
$Q^2$ is a saturated 4- to 6-membered heterocycle comprising a nitrogen atom;
$Q^3$ is —$CH_2$—;
$Q^4$ is a 5-membered aromatic heterocycle comprising 2 nitrogen atoms, said heterocycle being optionally substituted with methyl;
the atom of $Q^2$ bound to $Q^1$ is a carbon atom; and
the atom of $Q^4$ bound to $Q^3$ is a carbon atom.

6. A compound of claim 1 wherein $R^1$ is —Cl or —F.

7. A compound of claim 1 wherein m is 2.

8. A compound according to claim 1 and selected from the group consisting of:
5'-(2-[(2-amino-2-oxoethyl)amino]ethoxy)-8'-chloro-1'H-spiro[cyclohexane-1,4'-quinazolin]-2'(3'H)-one;
8'-chloro-5'-([methylsulfinyl]methoxy)-1'H-spiro[cyclohexane-1,4'-quinazolin]-2'(3'H)-one;
5'-(2-{[2-(acetylamino)ethyl]amino}ethoxy)-8'-chloro-1'H-spiro[cyclohexane-1,4'-quinazolin]-2'(3'H)-one;
8'-fluoro-5'-[3-(methylsulfinyl)propoxy]-1'H-spiro[cyclohexane-1,4'-quinazolin]-2'(3'H)-one;
8'-fluoro-5'-([methylsulfinyl]methoxy)-1'H-spiro[cyclohexane-1,4'-quinazolin]-2'(3'H)-one; and
8'-fluoro-5'-(2-{[1-(1H-pyrazol-3-ylmethyl)azetidin-3-yl]oxy})-1'H-sprio[cylclohexane-1,4'-quinazolin]-2'(3'H)-one.

9. A method of treating acquired immune deficiency syndrome (AIDS) in a mammal, comprising administering to said mammal in need thereof a compound of claim 1.

10. A pharmaceutical composition comprising a compound of claim 1 together with a pharmaceutically acceptable carrier, excipient, diluent or delivery system.

* * * * *